(12) United States Patent
Mihalik

(10) Patent No.: US 7,144,878 B2
(45) Date of Patent: *Dec. 5, 2006

(54) METHOD FOR TREATING ROUNDWORM INFESTATIONS IN ANIMALS

(75) Inventor: Richard Mihalik, St. Joseph, MO (US)

(73) Assignee: IVX Animal Health, Inc., St. Joseph, MO (US)

( * ) Notice: Subject to any disclaimer, the term of this patent is extended or adjusted under 35 U.S.C. 154(b) by 295 days.

This patent is subject to a terminal disclaimer.

(21) Appl. No.: 10/760,887

(22) Filed: Jan. 20, 2004

(65) Prior Publication Data

US 2004/0147462 A1    Jul. 29, 2004

Related U.S. Application Data

(60) Continuation of application No. 10/623,954, filed on Jul. 21, 2003, now Pat. No. 6,858,601, which is a division of application No. 09/723,846, filed on Nov. 28, 2000, now Pat. No. 6,596,714, which is a continuation of application No. 09/573,513, filed on May 18, 2000, now Pat. No. 6,207,179.

(51) Int. Cl.
*A01N 43/00* (2006.01)
*A01N 25/00* (2006.01)
*A61K 31/33* (2006.01)

(52) U.S. Cl. ........................ 514/183; 514/256; 424/405
(58) Field of Classification Search ................ 514/183, 514/256; 424/405
See application file for complete search history.

(56) References Cited

U.S. PATENT DOCUMENTS

| | | | | |
|---|---|---|---|---|
| 5,645,819 | A * | 7/1997 | Klapow | 424/45 |
| 6,596,714 | B1 * | 7/2003 | Mihalik | 514/183 |
| 6,858,601 | B1 * | 2/2005 | Mihalik | 514/183 |

* cited by examiner

*Primary Examiner*—Alton Pryor
(74) *Attorney, Agent, or Firm*—J. David Wharton; Stinson Morrison Hecker LLP

(57) ABSTRACT

A formulation for treating and preventing roundworm infestations in horses, dogs, cats, and other animals is provided. This formulation includes an agent effective against nematodes, wherein the agent is pyrantel, morantel, any salt thereof, or any combination thereof. Preferably, the formulation additionally includes an agent effective against nematodes and obligate parasitic flies, an edible non-aqueous liquid and a thickening agent. The formulation of the present invention allows for a high concentration of the agent effective against nematodes and for the treatment of roundworms, particularly ascarids, that have become resistant to at least one agent typically effective against nematodes.

29 Claims, No Drawings

METHOD FOR TREATING ROUNDWORM INFESTATIONS IN ANIMALS

CROSS-REFERENCE TO RELATED APPLICATIONS

This application is a continuation of U.S. patent application Ser. No. 10/623,954, filed Jul. 21, 2003 now U.S. Pat. No. 6,858,601, which is a divisional of U.S. patent application Ser. No. 09/723,846, filed on Nov. 28, 2000, which is now U.S. Pat. No. 6,596,714, which is a continuation of U.S. patent application Ser. No. 09/573,513, filed on May 18, 2000, which is now issued as U.S. Pat. No. 6,207,179. Each application and patent listed above is incorporated by reference in its entirety.

STATEMENT REGARDING FEDERALLY SPONSORED RESEARCH OR DEVELOPMENT

Not Applicable.

BACKGROUND OF THE INVENTION

The present invention relates to a formulation for treating, controlling and preventing parasitic worm infestations and a method for making the formulation. More specifically, the present invention relates to a combination roundworm and tapeworm parasiticide for use in horses and household pets.

Several types of parasites, including cestodes, nematodes and obligate parasitic insects, particularly flies, commonly plague horses, dogs and cats. Cestodes are flatworms and include, for example, tapeworms, while nematodes are roundworms. Avermectins and milbemycins are nematocidal agents commonly used in the treatment and control of parasitic roundworm infestations in equines, including domestic horses, donkeys, mules and zebras, as well as in companion animals, namely cats and dogs. These agents are also effective against obligate parasitic flies. Contrary to popular belief among animal owners, however, these agents are ineffective against tapeworm infestations. Rather, tapeworm infestations must be controlled and treated by a cestocidal agent.

Studies have shown that misinformation about tapeworm treatment and control is common among horse owners. Many horse owners evidently believe that ivermectin, an avermectin used for treating and controlling roundworm infestations, is effective in controlling tapeworm infestations as well. This misinformation may account for a rise in the prevalence of certain tapeworms. A particular equine tapeworm whose prevalence is on the rise is *Anoplocephala perfoliata*.

Tapeworms are pervasive parasites that appear to infect at least half of all mature horses. Post-mortem studies have shown that, in general, at least 50% of mature horses in many populations are infected with *A. perfoliata*. *A. perfoliata* is a type of tapeworm that can infect all types of equine animals. Adult *A. perfoliata* attach to the posterior regions of the equine intestinal tract. The highest concentration is in the cecal wall but a fair amount attach to the terminal ilium and ventral colon as well. The greatest concentration of *A. perfoliata*, and thus the greatest associated damage, occurs at the ileocecal junction. *A. perfoliata* infestation increases the incidence of spasmodic colon and ileal impaction in horses. Tapeworms also have been implicated as a cause of cecal and ileocecal intussusceptions in young horses. The latter conditions are potentially fatal and can be remedied only by complicated and expensive abdominal surgery.

There are only a few classes of drugs which are effective in the treatment, control and prevention of tapeworm infestations. Among these classes are praziquantel, pyrantel and morantel compounds. Parasiticidal formulations have been disclosed which contain praziquantel combined with a variety of roundworm controlling agents. One such formulation is disclosed in U.S. Pat. No. 5,824,653 to Beuvry et al. The compounds which result from these combinations, however, may be dangerous as praziquantel has been shown to be toxic at levels other than low dosages. Additionally, praziquantel purportedly is bitter to taste making it unpalatable and thus undesirable in ingestable formulations, for example, pastes.

Pyrantel and morantel compounds are currently believed by those skilled in the art to offer an inadequate substitute to praziquantel in the treatment and control of tapeworm infestations. Pyrantel salts generally either are only partially effective against tapeworms at their label dosages (e.g., pyrantel pamoate) or must be administered in daily regimes (e.g., pyrantel tartrate). Further, pyrantel pamoate offers a low suspended solids content when in paste form, the highest percentage encountered being about 43.95% weight per weight (w/w). A paste with a low suspended solids content contains less active ingredient per unit than a paste with a higher suspended solids content. Therefore, a higher volume of paste must be delivered to the animal in order to achieve the same therapeutic effect.

Accordingly, there remains a need in the veterinary industry for a combination parasiticidal formulation containing both a cestocidal agent and an agent effective against nematodes and obligate parasitic flies that is less toxic than formulations containing praziquantel. Further, a palatable combination parasiticide is needed for administration in ingestable forms. The primary objective of this invention is to meet these needs.

BRIEF SUMMARY OF THE INVENTION

According to the present invention, the foregoing and other objects are achieved by a parasiticidal formulation that includes a mixture of an edible non-aqueous liquid, a thickening agent, a first agent effective against nematodes and obligate parasitic flies and a second agent effective against nematodes and cestodes, wherein the second agent is pyrantel, morantel, any salt thereof, or any combination thereof. Preferably the first agent effective against nematodes and obligate parasitic flies is an avermectin, a milbemycin, a derivative thereof, or any combination thereof. Another aspect of the present invention is a method of making this parasiticidal formulation. This method includes mixing the above-mentioned components. A further aspect of the present invention is a method for administering the parasiticidal formulation of the present invention to an animal. This method of administration includes providing the parasiticidal formulation described above in the form of a paste and administering it to an animal for ingestion.

Objects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

The parasiticidal formulation of the present invention is an effective ingestable formulation for the treatment and control of cestode, nematode and obligate parasitic fly infestations in equine and companion animals. Such animals include, but are not limited to, horses, donkeys, mules, zebras, dogs and cats. The formulation includes an edible, non-aqueous liquid, a thickening agent, a first agent for treating and controlling roundworm and obligate parasitic fly infestations and a second agent, which is a cestocidal agent, for treating and controlling roundworm and tapeworm infestations. This mixture provides a unique formulation in which the agent effective against nematodes and obligate parasitic flies is allowed to dissolve substantially into solution while the cestocidal agent remains generally suspended. Thus, the system allows for delivery of two different parasiticidal agents in two different physical states simultaneously in a single oral formulation.

The second agent of the present invention includes pyrantel, morantel, any salt of pyrantel or morantel, or any combination thereof. These compounds offer advantages over praziquantel in the control and treatment of tapeworm infestations in that they have a higher dosage safety margin than praziquantel. Pyrantel pamoate, a salt of pyrantel, for example, should present little to no adverse reaction when ingested by horses in a concentration equivalent to two to five times the label recommended dosage. Further, pyrantels are desirable because horse owners are familiar with this group of compounds. Additionally, pyrantel and morantel are more palatable than praziquantel as these compounds do not share the bitter taste associated with praziquantel.

Preferably, the second agent of the present invention is a salt of pyrantel. Pyrantel salts that may be used in the formulation of the present invention include, but are not limited to, pyrantel pamoate, pyrantel tartrate or any combination thereof. Preferably, the second agent of the present invention is pyrantel pamoate. Pyrantel pamoate, at sufficiently high dosages, eliminates and controls infestations by a variety of tapeworms, including *Anoplocephala perfoliata*.

Pyrantel pamoate usually is classified as a nematocidal agent rather than a cestocidal agent at its recommended label dosage of about 6.6 milligrams per kilogram of animal. At this dosage, pyrantel pamoate has only partial activity in the treatment and control of tapeworm infestations. Effectiveness percentages from about 65% to 100% against cestode infestations have been shown with paste formulations, the average being about 85% efficacy. However, at about twice the label recommended dosage or higher, pyrantel pamoate exhibits tapeworm controlling activity unattainable by many cestocidal compounds at any dosage. It has been observed that at an elevated dosage of about two times the label recommended dosage, or about 13.2 milligrams per kilogram of animal, pyrantel pamoate exhibits between about 93% and 97.8% efficacy in horses infected with *A. perfoliata*. At an elevated dosage of about three times the label recommended dosage, or about 19.8 milligrams per kilogram of animal, pyrantel pamoate is about 100% effective in treating cestode infestations. Consequently, the parasiticidal formulation of the present invention includes concentrations of pyrantel pamoate at about two to three times the dosage recommended for treatment and control of roundworm infestations.

When the cestocidal agent chosen is pyrantel pamoate, the formulation of the present invention preferably may include about 40–75% w/w pyrantel pamoate (a total of about 14–26% w/w pyrantel in the formulation). More preferably, the formulation of the present invention may include about 50–65% w/w pyrantel pamoate (a total of about 17–23% w/w pyrantel in the formulation). Formulations containing other cestocidal agents besides pyrantel pamoate are also contemplated by this invention, as discussed above. If a different pyrantel compound is used, preferably the formulation would contain pyrantel in an amount similar to the amounts discussed above.

As noted above, at elevated dosages, pyrantel pamoate serves both as a nemotocidal agent and a cestocidal agent. Additional agents which are effective against nematodes and obligate parasitic flies that may be used in the formulation of the present invention include, but are not limited to, avermectins, milbemycins, any derivative thereof, or any combination thereof. Avermectins that may be used in the formulation of the present invention include, but are not limited to, abamectin, doramectin, eprinomectin, ivermectin, moxidectin, selamectin, or any combination thereof. These agents are most effective when substantially dissolved in solution, i.e., when at least about 90% of the agent present is dissolved. Thus, it is preferred that these agents be combined with a solvent before being administered to an animal. Preferably the first agent used in the formulation of the present invention is ivermectin. Ivermectin kills a variety of roundworms including stomach worms, intestinal worms, lungworms, barber's pole worms, lice and mites, as well as bots and grubs of obligate parasitic flies.

When the first agent chosen is ivermectin, the formulation of the present invention preferably may include about 0.10–10% w/w ivermectin. More preferably, the formulation of the present invention may include about 0.25–0.35% w/w ivermectin.

When using ivermectin and pyrantel pamoate in combination, the parasiticidal formulation of the present invention preferably may include about 0.2–1.0% w/w ivermectin and about 45–65% w/w pyrantel pamoate. More preferably, the formulation of the present invention may include about 0.2–0.5% w/w ivermectin and about 50–60% w/w pyrantel pamoate.

The edible, non-aqueous liquid that may be used in the formulation of the present invention includes, but is not limited to, edible glycol polymers, edible oils, or any combination thereof. Edible glycol polymers that may be used in the formulation of the present invention include, but are not limited to, propylene glycol, polyethylene glycol, glycerine (glycerol), glycerol formal, or any combination thereof. Edible oils that may be used in the formulation of the present invention include, but are not limited to, Arachis oil (peanut oil), polyoxyl castor oils, soybean oil, or any combination thereof. Preferably, the edible, non-aqueous liquid is propylene glycol.

The edible, non-aqueous liquid preferably is present in the parasiticidal formulation of the present invention in an amount effective, in combination with the thickening agent, for substantially dissolving a therapeutic amount of one or more agents effective against nematodes and obligate parasitic flies while allowing one or more cestocidal agents to remain generally suspended. The agents effective against nematodes and obligate parasitic flies are substantially dissolved in solution when at least about 90% of the agent present is dissolved. Cestocidal agents are generally suspended when less than about 10% of the agent present is dissolved. The formulation of the present invention preferably may include a total of about 40–50% w/w edible, non-aqueous liquid. More preferably, the formulation of the present invention may include about 42–46% w/w edible, non-aqueous liquid.

The thickening agent that may be used in the formulation of the present invention includes, but is not limited to, carbomers, cornstarch, polyethylene, polyvinylpyrrolidones, edible clay, xanthan gum, or any combination thereof. Preferably, the thickening agents are a carbomer and xanthan gum. A suitable carbomer is Carbomer 974P manufactured by B.F. Goodrich. The thickening agent preferably includes an amount that is effective, in combination with the edible, non-aqueous liquid, to substantially dissolve a therapeutic amount of one or more agents effective against nematodes and obligate parasitic flies (preferably at least about 90% dissolved) while allowing one or more cestocidal agents to remain generally suspended (preferably less than about 10% dissolved). The formulation of the present invention preferably may include about 0.01–1.0% w/w thickening agent. More preferably, the formulation of the present invention may include about 0.09–0.65% w/w thickening agent.

The combination of an edible, non-aqueous liquid and a thickening agent to form the unique system of the present invention allows one or more cestocidal agents to dissolve substantially while allowing one or more agents effective against nematodes and obligate parasitic flies to remain generally suspended. As a result, the system of the present invention allows for delivery of two different parasiticidal agents in two different physical states simultaneously in a single oral formulation. The combination of the edible, non-aqueous liquid and the thickening agent also functions to transport one or more cestocidal agents and one or more agents effective against nematodes and obligate parasitic flies into an animal in the physical state in which each is most effective so that the agents may interact therapeutically with parasites in the animal. In animals with no parasite infestations upon administration, the combination of the edible, non-aqueous liquid and the thickening agent functions to transport one or more cestocidal agents and one or more agents effective against nematodes and obligate parasitic flies into an animal in the physical state in which each is most effective so that the animal is protected from subsequent infestations by certain parasites.

Further, the formulation of the present invention allows for higher suspended solids content for some cestocidal agents than was foreseen as being possible from the prior art. For example, the formulation of the present invention allows for a paste containing pyrantel pamoate having a suspended solids content of up to about 70% w/w, with a preferred concentration of about 54.13% w/w. The highest concentration previously encountered in a paste containing pyrantel was about 43.95% w/w. The higher suspended solids content allows for a significantly smaller volume of paste to be administered, making it easier to deliver higher dosages of pyrantel than when previously available formulations are used.

As discussed above, cestocidal agents and agents effective against nematodes and obligate parasitic flies each provide protection against different species of parasites. Thus, when a cestocidal agent and an agent effective against nematodes and obligate parasitic flies are combined in a single parasiticidal formulation, the formulation provides protection against a broader spectrum of parasites than a formulation containing either parasiticidal agent alone. The parasiticidal formulation of the present invention may be administered either to treat infected animals or to prevent infestations in non-infected animals. Preferably, the formulation is administered once per month.

A number of optional ingredients may be added to enhance certain properties of the formulation. One such optional ingredient is a preservative which acts to preserve both parasiticidal agents in the physical state in which they are most effective. Preservatives that may be used in the formulation of the present invention include, but are not limited to, methylparaben, propylparaben, or any combination thereof. Preferably, the formulation of the present invention includes a combination of methylparaben and propylparaben in a ratio of approximately 10:1 respectively. If a combination of methylparaben and propylparaben is chosen as a preservative for the formulation, the parasiticidal formulation of the present invention preferably may include about 0.15–0.25% w/w methylparaben and about 0.015–0.025% w/w propylparaben. More preferably, the parasiticidal formulation of the present invention may include about 0.18% w/w methylparaben and about 0.02% w/w propylparaben.

Another optional ingredient that may be included in the formulation of the present invention is an additional solvent for the agent effective against nematodes and obligate parasitic flies. Preferably this solvent is water. Water may be present in a concentration ranging from about 0–10% w/w depending upon the concentration of edible, non-aqueous liquid used. The total amount of solvent should be sufficient to dissolve substantially all of the agent effective against nematodes and obligate parasitic flies present in the formulation of the present invention while allowing all of the cestocidal agent to remain generally suspended.

One preferred formulation of the present invention includes pyrantel pamoate, ivermectin, xanthan gum, carbomer, methylparaben, propylparaben and propylene glycol. Another preferred formulation of the present invention includes pyrantel pamoate, ivermectin, xanthan gum, carbomer and propylene glycol. A highly preferred formulation of the present invention which includes a preservative is described in Example 1. A highly preferred formulation of the present invention which does not include a preservative is described in Example 2.

One parasiticidal formulation of the present invention is made by combining an edible non-aqueous liquid, a thickening agent, a first agent effective against nematodes and obligate parasitic flies and a second agent effective against nematodes and cestodes to form a mixture. Preferably, ivermectin and pyrantel pamoate may be used respectively. The order in which components are added in making the formulation is not critical. The formulation may optionally be heated to between about 60° and 80° C., continuously or intermittently, during its preparation in order to dissolve the agent effective against nematodes and obligate parasitic flies more quickly. This process can be scaled to make any desired quantity of the formulation.

One preferred method of making a parasiticidal formulation of the present invention includes placing a quantity of edible, non-aqueous liquid in a vessel and warming it to about 70° C. Next, a quantity of a first agent effective against nematodes and obligate parasitic flies is added, and the resulting solution is cooled to room temperature. The second agent effective against nematodes and cestodes is then added and mixed with the solution for an effective period of time. The second agent will not dissolve into solution but instead will remain generally suspended throughout, i.e., less than about 10% will dissolve. A thickening agent is then added and mixed into the solution until it dissolves substantially, i.e., until at least 90% of the thickening agent present is dissolved. Optionally, a preservative then may be added and mixed into the solution until substantially dissolved, i.e., until at least 90% of the preservative present is dissolved.

Preferably, the parasiticidal formulation of the present invention is administered as a paste formulation to any equine or companion animal. It is particularly useful for domestic horses, donkeys, mules, zebras, cats and dogs. Preferably, the paste is ingested by the animal and is administered in a dosage of about 65–75 milligrams per kilogram of animal once per month.

The following are examples of various parasiticidal formulations and methods of making these formulations that are within the scope of this invention. These examples are not meant in any way to limit the scope of this invention.

EXAMPLE 1

Propylene glycol, in a quantity amounting to 44.17% w/w of the final formulation, was added to a vessel and warmed to 70° C. Agitation began. With continued agitation, a quantity of ivermectin amounting to 0.29% w/w of the final formulation was added to the propylene glycol and mixed with it until all of the ivermectin substantially dissolved. The resulting solution was then cooled to room temperature. A quantity of pyrantel pamoate amounting to 55.14% w/w of the final formulation (19.13% w/w of final formulation as pyrantel) was then added and mixed with the solution. The pyrantel pamoate did not dissolve in the solution but instead remained generally suspended throughout. Next, a quantity of xanthan gum amounting to 0.18% w/w of the final formulation was added to the mixture. With continued agitation, Carbomer 974P was added to the mixture in a quantity amounting to 0.02% w/w of the final formulation. Subsequently, methylparaben, in a quantity amounting to 0.18% w/w of the final formulation, was added to the mixture, followed by a quantity of propylparaben amounting to 0.02% w/w of the final formulation. The resulting formulation is within the scope of the present invention and includes two parasiticidal agents, each targeting different species of parasites.

EXAMPLE 2

Propylene glycol, in a quantity amounting to 44.37% w/w of the final formulation, was added to a vessel and warmed to 70° C. Agitation began. With continued agitation, a quantity of ivermectin amounting to 0.29% w/w of the final formulation was added to the propylene glycol and mixed with it until all of the ivermectin substantially dissolved. The resulting solution was then cooled to room temperature. A quantity of pyrantel pamoate amounting to 55.14% w/w of the final formulation (19.13% w/w of final formulation as pyrantel) was then added and mixed with the solution. The pyrantel pamoate did not dissolve in the solution but instead remained generally suspended throughout. With continued agitation, a quantity of xanthan gum amounting to 0.18% w/w of the final formulation was added to the mixture. Subsequently, carbomer 974P was added to the mixture in a quantity amounting to 0.02% w/w of the final formulation. The resulting formulation is within the scope of the present invention and includes two parasiticidal agents, each targeting different species of parasites.

EXAMPLE 3

Propylene glycol, in a quantity amounting to 30% w/w of the final formulation, was added to a vessel and warmed to 70° C. Agitation began. With continued agitation, water in a quantity amounting to 7.285% w/w of the final formulation, was added to the propylene glycol to form a solution. Next, a quantity of ivermectin amounting to 0.325% w/w of the final formulation was added to the solution and mixed with it until all of the ivermectin substantially dissolved. The resulting solution was then cooled to room temperature. A quantity of pyrantel pamoate amounting to 61.74% w/w of the final formulation (21.42% w/w of final formulation as pyrantel) was then added and mixed with the solution. The pyrantel pamoate did not dissolve in the solution but instead remained generally suspended throughout. Lastly, a quantity of xanthan gum amounting to 0.65% w/w of the final formulation was added to the mixture. The resulting formulation is within the scope of the present invention and includes two parasiticidal agents, each targeting different species of parasites.

EXAMPLE 4

Propylene glycol, in a quantity amounting to 28% w/w of the final formulation, was added to a vessel and warmed to 70° C. Agitation began. With continued agitation, water, in a quantity amounting to 9.285% w/w of the final formulation, was added to the propylene glycol to form a solution. Next, ivermectin amounting to 0.325% w/w of the final formulation was added to the solution and mixed with it until all of the ivermectin substantially dissolved. The resulting solution was then cooled to room temperature. A quantity of pyrantel pamoate amounting to 61.74% w/w of the final formulation (21.42% w/w of final formulation as pyrantel) was then added and mixed with the solution. The pyrantel pamoate did not dissolve in the solution but instead remained generally suspended throughout. Lastly, a quantity of xanthan gum amounting to 0.65% w/w of the final formulation was added to the mixture. The resulting formulation is within the scope of the present invention and includes two parasiticidal agents, each targeting different species of parasites.

EXAMPLE 5

Propylene glycol, in a quantity amounting to 32.0% w/w of the final formulation, was added to a vessel and warmed to 70° C. Agitation began. With continued agitation, water, in a quantity amounting to 5.285% w/w of the final formulation, was added to the propylene glycol to form a solution. Next, ivermectin amounting to 0.325% w/w of the final formulation was added to the solution and mixed with it until all of the ivermectin substantially dissolved. The resulting solution was then cooled to room temperature. A quantity of pyrantel pamoate amounting to 61.74% w/w of the final formulation (21.42% w/w of final formulation as pyrantel) was then added and mixed with the solution. The pyrantel pamoate did not dissolve in the solution but instead remained generally suspended throughout. Lastly, a quantity of xanthan gum amounting to 0.65% w/w of the final formulation was added to the mixture. The resulting formulation is within the scope of the present invention and includes two parasiticidal agents, each targeting different species of parasites.

EXAMPLE 6

Propylene glycol, in a quantity amounting to 37.836% w/w of the final formulation, was added to a vessel and warmed to 70° C. Agitation began. With continued agitation, water, in a quantity amounting to 7.0% w/w of the final formulation, was added to the propylene glycol to form a solution. Next, ivermectin amounting to 0.284% w/w of the final formulation was added to the solution and mixed with it until all of the ivermectin substantially dissolved. The resulting solution was then cooled to room temperature. A quantity of pyrantel pamoate amounting to 54.03% w/w of the final formulation (18.75% w/w of final formulation as pyrantel) was then added and mixed with the solution. The pyrantel pamoate did not dissolve in the solution but instead remained generally suspended throughout. With continued agitation, a quantity of xanthan gum amounting to 0.65% w/w of the final formulation was added to the mixture. Lastly, Carbomer 974P was added to the mixture in a quantity amounting to 0.02% w/w of the final formulation. The resulting formulation is within the scope of the present invention and includes two parasiticidal agents, each targeting different species of parasites.

EXAMPLE 7

Propylene glycol, in a quantity amounting to 44.806% w/w of the final formulation, was added to a vessel and warmed to 70° C. Agitation began. With continued agitation, water, in a quantity amounting to 0.48% w/w of the final formulation, was added to the propylene glycol to form a solution. Next, ivermectin amounting to 0.284% w/w of the final formulation was added to the solution and mixed with it until all of the ivermectin substantially dissolved. The resulting solution was then cooled to room temperature. With continued agitation, a quantity of pyrantel pamoate amounting to 54.03% w/w of the final formulation (18.75% w/w of final formulation as pyrantel) was then added and mixed with the solution. The pyrantel pamoate did not dissolve in the solution but instead remained generally suspended throughout. Next, a quantity of xanthan gum amounting to 0.2% w/w of the final formulation was added to the mixture. Lastly, Carbomer 974P was added to the mixture in a quantity amounting to 0.2% w/w of the final formulation. The resulting formulation is within the scope of the present invention and includes two parasiticidal agents, each targeting different species of parasites.

EXAMPLE 8

Propylene glycol, in a quantity amounting to 43.4% w/w of the final formulation, was added to a vessel and warmed to 70° C. Agitation began. With continued agitation, a quantity of ivermectin amounting to 0.275% w/w of the final formulation was added to the propylene glycol and mixed with it until all of the ivermectin substantially dissolved. The resulting solution was then cooled to room temperature. A quantity of pyrantel pamoate amounting to 56.17% w/w of the final formulation (19.49% w/w of final formulation as pyrantel) was then added and mixed with the solution. The pyrantel pamoate did not dissolve in the solution but instead remained generally suspended throughout. With continued agitation, a quantity of xanthan gum amounting to 0.097% w/w of the final formulation was added to the mixture. Lastly, Carbomer 974P was added to the mixture in a quantity amounting to 0.097% w/w of the final formulation. The resulting formulation is within the scope of the present invention and includes two parasiticidal agents, each targeting different species of parasites.

EXAMPLE 9

Propylene glycol, in a quantity amounting to 44.14% w/w of the final formulation, was added to a vessel and warmed to 70° C. Agitation began. With continued agitation, a quantity of ivermectin amounting to 0.29% w/w of the final formulation was added to the propylene glycol and mixed with it until all of the ivermectin substantially dissolved. The resulting solution was then cooled to room temperature. A quantity of pyrantel pamoate amounting to 55.17% w/w of the final formulation (19.14% w/w of final formulation as pyrantel) was then added and mixed with the solution. The pyrantel pamoate did not dissolve in the solution but instead remained generally suspended throughout. Next, a quantity of xanthan gum amounting to 0.1% w/w of the final formulation was added to the mixture. With continued agitation, Carbomer 974P was added to the mixture in a quantity amounting to 0.1% w/w of the final formulation. Subsequently, methylparaben, in a quantity amounting to 0.18% w/w of the final formulation, was added to the mixture, followed by a quantity of propylparaben amounting to 0.02% w/w of the final formulation. The resulting formulation is within the scope of the present invention and includes two parasiticidal agents, each targeting different species of parasites.

EXAMPLE 10

Propylene glycol, in a quantity amounting to 49.705% w/w of the final formulation, was added to a vessel and warmed to 70° C. Agitation began. With continued agitation, a quantity of ivermectin amounting to 0.235% w/w of the final formulation was added to the propylene glycol and mixed with it until all of the ivermectin substantially dissolved. The resulting solution was then cooled to room temperature. A quantity of pyrantel pamoate amounting to 49.7% w/w of the final formulation (17.25% w/w of final formulation as pyrantel) was then added and mixed with the solution. The pyrantel pamoate did not dissolve in the solution but instead remained generally suspended throughout. Next, a quantity of xanthan gum amounting to 0.135% w/w of the final formulation was added to the mixture. With continued agitation, Carbomer 974P was added to the mixture in a quantity amounting to 0.045% w/w of the final formulation. Subsequently, methylparaben, in a quantity amounting to 0.162% w/w of the final formulation, was added to the mixture, followed by a quantity of propylparaben amounting to 0.018% w/w of the final formulation. The resulting formulation is within the scope of the present invention and includes two parasiticidal agents, each targeting different species of parasites.

EXAMPLE 11

Propylene glycol, in a quantity amounting to 38.199% w/w of the final formulation, was added to a vessel and warmed to 70° C. Agitation began. With continued agitation, a quantity of sterile water in a quantity amounting to 6.0% w/w of the final formulation was added to the propylene glycol to form a solution. Next, ivermectin amounting to 0.261% w/w of the final formulation was added to the solution and mixed with it until all of the ivermectin substantially dissolved. The resulting solution was then cooled to room temperature. A quantity of pyrantel pamoate amounting to 55.14% w/w of the final formulation (19.13% w/w of final formulation as pyrantel) was then added and mixed with the solution. The pyrantel pamoate did not dissolve in the solution but instead remained generally suspended throughout. With continued agitation, a quantity of xanthan gum amounting to 0.1% w/w of the final formulation was added to the mixture. With continued agitation, a quantity of Carbomer 974P was added to the mixture in a quantity amounting to 0.1% w/w of the final formulation. Lastly, methylparaben, in a quantity amounting to 0.18% w/w of the final formulation, was added to the mixture, followed by a quantity of propylparaben amounting to 0.02% w/w of the final formulation. The resulting formulation is within the scope of the present invention and includes two parasiticidal agents, each targeting different species of parasites.

EXAMPLE 12

Propylene glycol, in a quantity amounting to 44.19% w/w of the final formulation, was added to a vessel and warmed to 70° C. Agitation began. With continued agitation, a quantity of ivermectin amounting to 0.261% w/w of the final formulation was added to the propylene glycol and mixed with it until all of the ivermectin substantially dissolved. The resulting solution was then cooled to room temperature. A quantity of pyrantel pamoate amounting to 55.14% w/w of the final formulation (19.13% w/w of final formulation as pyrantel) was then added and mixed with the solution. The pyrantel pamoate did not dissolve in the solution but instead remained generally suspended throughout. Next, a quantity of xanthan gum amounting to 0.15% w/w of the final formulation was added to the mixture. With continued agitation, Carbomer 974P was added to the mixture in a quantity amounting to 0.05% w/w of the final formulation. Lastly, methylparaben, in a quantity amounting to 0.18% w/w of the final formulation, was added to the mixture, followed by a quantity of propylparaben amounting to 0.02% w/w of the final formulation. The resulting formulation is within the scope of the present invention and includes two parasiticidal agents, each targeting different species of parasites.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, is to be understood that all matters herein set forth are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and sub-combinations are of utility and may be employed without reference to other features and sub-combinations. This is contemplated by and is within the scope of the claims.

I claim:

1. A method of treating infestations of roundworms in animals, comprising:
    providing a parasiticidal formulation comprising a mixture of (i) an edible non-aqueous liquid, (ii) a thickening agent, (iii) a first agent effective against nematodes and obligate parasite flies, and (iv) a second agent effective against nematodes, wherein said second agent is selected from the group consisting of pyrantel, morantel, any salt thereof and any combination thereof; and
    orally administering said formulation as a paste to said animal in an amount therapeutically effective against said roundworms.

2. The method of claim 1, wherein said roundworms are ascarids, and wherein said formulation is administered in an amount therapeutically effective against said ascarids.

3. The method of claim 2, wherein said first agent is an avermectin.

4. The method of claim 3, wherein said ascarids are resistant to avermectins, and wherein said formulation is administered in an amount therapeutically effective against said avermectin-resistant ascarids.

5. The method of claim 4, wherein said ascarids are resistant to ivermectin, and wherein said formulation is administered in an amount therapeutically effective against said ivermectin-resistant ascarids.

6. The method of claim 5, wherein said formulation is orally administered to a horse.

7. The method of claim 5, wherein said second agent is pyrantel or a salt thereof.

8. The method of claim 7, wherein said first agent is ivermectin.

9. The method of claim 1, wherein said roundworms are resistant to avermectins, and wherein said formulation is administered in an amount therapeutically effective against said averemectin-resistant roundworms.

10. The method of claim 9, wherein said roundworms are resistant to ivermectin, and wherein said formulation is administered in an amount therapeutically effective against said ivermectin-resistant roundworms.

11. The method of claim 9, wherein said second agent is effective against cestodes.

12. The method of claim 1, wherein said second agent is present in said formulation in an amount equal to or greater than about 17% w/w.

13. The method of claim 1, wherein said second agent is present as a salt, and said salt is present in said formulation in an amount equal to or greater than about 50% w/w.

14. A method of treating infestations of roundworms in animals, comprising:
    providing a parasiticidal formulation comprising an agent effective against nematodes, wherein said agent is selected from the group consisting of pyrantel, morantel, and combinations thereof, an edible, non-aqueous liquid, wherein said agent is present in said formulation in an amount equal to or greater than about 17% w/w; and wherein said formulation comprises no more than about 10% w/w water; and
    administering said formulation to said animal in an amount therapeutically effective against said roundworms.

15. The method of claim 14, wherein said roundworms are ascarids, and wherein said formulation is administered in an amount therapeutically effective against said ascarids.

16. The method of claim 15, wherein said ascarids are resistant to avermectins, and wherein said formulation is administered in an amount therapeutically effective against said avermectin-resistant ascarids.

17. The method of claim 16, wherein said ascarids are resistant to ivermectin, and wherein said formulation is administered in an amount therapeutically effective against said ivermectin-resistant ascarids.

18. The method of claim 17, wherein said agent is present in said formulation in an amount equal to or greater than about 19% w/w.

19. The method of claim 18, wherein said agent is present as a salt, and said salt is present in said formulation in an amount equal to or greater than about 50% w/w.

20. The method of claim 19, wherein said salt is selected from the group consisting of pyrantel pamoate, pyrantel tartrate and any combination thereof.

21. The method of claim 20, wherein said salt is pyrantel pamoate.

22. The method of claim 17, wherein said formulation is administered to a horse.

23. The method of claim 17, wherein said formulation is administered orally.

24. The method of claim 23, wherein said formulation is a paste.

25. The method of claim 24, wherein said animal is a horse.

26. A method of treating infestations of roundworms in animals, comprising:
  providing a parasiticidal formulation comprising a mixture of (i) an edible non-aqueous liquid that is an edible oil selected from the group consisting of Arachis oil, polyoxyl castor oil, soybean oil and any combination thereof, (ii) a thickening agent, (iii) a first agent effective against nematodes and obligate parasite flies, and (iv) a second agent effective against nematodes, wherein said second agent is selected from the group consisting of pyrantel, morantel, any salt thereof and any combination thereof; and
  administering said formulation to said animal in an amount therapeutically effective against said roundworms.

27. A method of treating infestations of roundworms in animals, comprising:
  providing a parasiticidal formulation comprising a mixture of (i) an edible non-aqueous liquid that is an edible oil glycol polymer selected from the group consisting of propylene glycol, polyethylene glycol, glycerine, glycerol formal and any combination thereof, wherein said non-aqueous liquid is comprised of about 25–55% weight per weight proplylene glycol, (ii) a thickening agent, (iii) a first agent effective against nematodes and obligate parasite flies, and (iv) a second agent effective against nematodes, wherein said second agent is selected from the group consisting of pyrantel, morantel, any salt thereof and any combination thereof; and
  administering said formulation to said animal in an amount therapeutically effective against said roundworms.

28. A method of treating infestations of roundworms in animals, comprising:
  providing a parasiticidal formulation comprising a mixture of (i) an edible non-aqueous liquid, (ii) a thickening agent selected from the group consisting of a carbomer, cornstarch, polyethylene, a polyvinylpyrrolidone, and edible clay, xanthan gum and any combination thereof, (iii) a first agent effective against nematodes and obligate parasite flies, and (iv) a second agent effective against nematodes, wherein said second agent is selected from the group consisting of pyrantel, morantel, any salt thereof and any combination thereof; and
  administering said formulation to said animal in an amount therapeutically effective against said roundworms.

29. A method of treating infestations of roundworms in animals, comprising:
  providing a parasiticidal formulation comprising a mixture of (i) an edible non-aqueous liquid, (ii) a thickening agent, (iii) a first agent effective against nematodes and obligate parasite flies, (iv) a second agent effective against nematodes, wherein said second agent is selected from the group consisting of pyrantel, morantel, any salt thereof and any combination thereof, and (v) a preservative selected from the group consisting of methylparaben, propylparaben and any combination thereof; and
  administering said formulation to said animal in an amount therapeutically effective against said roundworms.

* * * * *